(12) United States Patent
Gouma et al.

(10) Patent No.: US 11,467,459 B2
(45) Date of Patent: Oct. 11, 2022

(54) ELECTROCHROMIC DEVICES AND METHODS

(71) Applicant: Board of Regents, The University of Texas System, Austin, TX (US)

(72) Inventors: Pelagia I. Gouma, Columbus, OH (US); Owen Oladele Abe, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 720 days.

(21) Appl. No.: 16/268,094

(22) Filed: Feb. 5, 2019

(65) Prior Publication Data
US 2019/0243203 A1    Aug. 8, 2019

Related U.S. Application Data

(60) Provisional application No. 62/626,444, filed on Feb. 5, 2018.

(51) Int. Cl.
| | | |
|---|---|---|
| G02F 1/1524 | (2019.01) | |
| G02F 1/155 | (2006.01) | |
| C01G 41/02 | (2006.01) | |
| G01N 21/78 | (2006.01) | |
| G01N 33/497 | (2006.01) | |

(52) U.S. Cl.
CPC .......... *G02F 1/1524* (2019.01); *C01G 41/02* (2013.01); *G01N 21/78* (2013.01); *G01N 33/497* (2013.01); *G02F 1/155* (2013.01); C01P 2002/72 (2013.01); C01P 2002/82 (2013.01); C01P 2002/90 (2013.01); C01P 2004/64 (2013.01); C01P 2006/60 (2013.01); G01N 2033/4975 (2013.01); G02F 2202/36 (2013.01)

(58) Field of Classification Search
None
See application file for complete search history.

(56) References Cited

U.S. PATENT DOCUMENTS

| | | | | |
|---|---|---|---|---|
| 2009/0148347 | A1* | 6/2009 | Lee | C23C 14/08 422/83 |
| 2013/0329179 | A1* | 12/2013 | Cook | B82Y 30/00 349/182 |
| 2015/0346190 | A1* | 12/2015 | Sambandan | G01N 33/497 73/23.3 |

* cited by examiner

*Primary Examiner* — Lore R Jarrett
(74) *Attorney, Agent, or Firm* — John H. Bieber (57) ABSTRACT

An electrochromic device comprising a substrate, a set of electrodes disposed on or within the substrate, and a layer comprising ε-$WO_3$ disposed in electrical communication with the set of electrodes, wherein the layer of ε-$WO_3$ exhibits polarization switching are described. Methods of making and using the electrochromic devices are also described. The electrochromic devices are used for detecting acetone in a fluid. The observed change in color of the ε-$WO_3$ layer can be correlated with a subject's medical condition, such as diabetes.

10 Claims, 3 Drawing Sheets

ELECTROCHROMIC DEVICES AND METHODS

CROSS-REFERENCE TO RELATED APPLICATIONS

This application claims benefit of U.S. Provisional Application No. 62/626,444, filed Feb. 5, 2018, which is hereby incorporated herein by reference in its entirety.

STATEMENT REGARDING FEDERALLY SPONSORED RESEARCH

This invention was made with Government Support under Grant No. DMR 1724455 awarded by the National Science Foundation. The Government has certain rights in the invention.

FIELD

The present invention relates to electrochromic devices and methods, and, more particularly, to electrochromic devices comprising epsilon phase tungsten trioxide ($\epsilon$-$WO_3$) and methods of making and using the same.

BACKGROUND

Electrochromic materials exhibit reversible changes in optical properties, such as, for example, reflectance, absorbance, and/or transmittance in the presence of an applied voltage. Tungsten trioxide ($WO_3$) is a known electrochromic material that exhibits a range of colors stimulated by redox reactions induced by changes in the applied voltage. The electrochromism of $WO_3$ can be attributed, in part, to the intercalation and deintercalation of ions respective to the $WO_3$ crystals during voltage switching. While lithium ion ($Li^+$) intercalation generally accompanies electrochromic color shifts in $WO_3$, the charge-balancing counter flow of electrons associated with the intercalation and deintercalation leads to a change in the electron density of $WO_3$ and, thus, changes in coloration and/or other optical effects.

Currently, electrochromic devices that utilize $WO_3$ require both an ion storage layer and an electrolytic layer to induce coloration changes via the redistribution of charges and ion flow associated with intercalation and deintercalation. Inclusion of such layers in an electrochromic device is problematic, however, from a cost, design, and ease of manufacture standpoint. Moreover, the provision of lithium in electrochromic devices can adversely affect humans and the environment.

Accordingly, a need exists for improved electrochromic devices and methods of making and using the same.

SUMMARY

The subject matter herein provides for improved electrochromic devices and methods of making and using the same. Such devices and methods advantageously incorporate epsilon phase tungsten trioxide ($\epsilon$-$WO_3$), and are devoid of ion storage layers, electrolyte and/or electrolytic layers, and/or lithium or other metals for promoting electrochromism.

Without being bound by theory, it is believed that the reversible coloration of the electrochromic devices described herein is resultant from the asymmetric ferroelectric properties associated with $\epsilon$-$WO_3$, such properties being coupled with the polarization switching of the devices. Accordingly, the devices set forth herein exhibit both electrochromic and ferroelectric properties suitable for use in a variety of switching applications. The electrochromic devices described herein are simpler, less expensive, and easier to manufacture than existing devices. Moreover, the electrochromic devices and methods of making and using the same devices do not rely on intercalation/deintercalation of hydrogen, lithium, or other ions in the electrochromic layer.

In one aspect, an electrochromic device is provided. Such a device comprises at least one set of electrodes such as interdigitated electrodes and a layer of $WO_3$ disposed on, over, or in contact with the electrodes. The layer of $WO_3$ is in electrical communication with the electrodes, and comprises up to 100% $\epsilon$-$WO_3$, based on the total weight of the layer of $WO_3$. The layer of $WO_3$ further exhibits polarization switching. Additionally, a layer of $WO_3$ described herein can exhibit asymmetric ferroelectric behavior.

In some embodiments, the layer of $WO_3$ comprises nanoparticles of $\epsilon$-$WO_3$ having an average size of up to 100 nm in at least two dimensions. In further embodiments, the layer of $WO_3$ comprises nanoparticles of $\epsilon$-$WO_3$ having an average size of up to 60 nm in three dimensions. Moreover, in some cases, the average size (in two or three dimensions) of particles forming a layer of $\epsilon$-$WO_3$ described herein is no larger than the ferroelectric domain size for the material.

Additionally, the layer of $WO_3$ can comprise pure $\epsilon$-$WO_3$, doped $\epsilon$-$WO_3$, or a mixed phase of $\epsilon$-$WO_3$. In cases where the layer of $WO_3$ is doped, it may be doped with silicon and/or chromium.

In further embodiments, the layer of $WO_3$ does not include and/or is substantially devoid of intercalated ions, such as hydrogen or lithium ions. Moreover, the intercalated ions of the layer of $WO_3$ do not determine a color of the layer of $WO_3$ and/or a color change exhibited by the layer of $WO_3$. That is, the colorization of the layer of $WO_3$, is not driven by the intercalation of ions.

In other respects, the layer of $WO_3$ is electrochromic and switches between a colored state and a bleached state in response to an applied bias between the electrodes such as between the interdigitated electrodes. In the colored state, for example, the layer of $WO_3$ exhibits a uniform or substantially uniform color distribution. Alternatively, the layer of $WO_3$ may exhibit a non-uniform color distribution. For example, in certain cases, the color distribution is locally disposed or distributed proximate to the electrodes, or is a function of the distance from the electrodes.

Furthermore, in some cases, the layer of $WO_3$ is disposed on a substrate. The substrate may be translucent and/or transparent. Alternatively, the substrate may be opaque. Exemplary substrates include or are formed from, for example, and without limitation, glass, ceramic, paper, plastic, or any combination thereof.

Notably, the devices set forth herein do not include and/or are devoid of an ion storage layer. Further, such devices do not include and/or are devoid of an electrolytic layer.

Electrochromic windows, mirrors, and/or displays can comprise, consist, or consist essentially of the devices described herein. Further, non-volatile memory elements can comprise, consist, or consist essentially of the devices described herein.

In a further aspect, a method of making an electrochromic device is provided. Such a method comprises forming a layer of $WO_3$, wherein the layer contains primarily $\epsilon$-$WO_3$, and placing the layer of $WO_3$ in electrical communication with a set of electrodes (e.g., interdigitated electrodes). The layer of $WO_3$ exhibits polarization switching. Additionally, the layer of $WO_3$ can be formed via flame spray pyrolysis, laser pyrolysis, high energy ball milling, or a rapid solidification process.

The present disclosure further provides a method for acetone detection in a fluid using the electrochromic devices described herein. The devices comprising $\varepsilon\text{-}WO_3$ shows appreciable sensitivity at 10 ppm acetone concentration or less. The present disclosure provides a device and method for acetone detection in breath for diabetics.

The details of one or more embodiments of the invention are set forth in the accompanying drawings and the description below. Other features, objects, and advantages of the invention will be apparent from the description and drawings, and from the claims.

DETAILED DESCRIPTION

Embodiments described herein can be understood more readily by reference to the following detailed description, examples, and figures. The electrochromic devices and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with a given amount or quantity, it is to be understood that the amount is at least a detectable amount or Quantity. For example, a material present in an amount "up to" a specified amount can be present from a detectable amount and up to and including the specified amount.

Electrochromic Devices

In one aspect, electrochromic devices are provided. Such devices comprise a plurality of electrodes and least one layer of $WO_3$ comprising up to 100% of $\varepsilon\text{-}WO_3$. Without being bound by theory, it is believed that changes in coloration and/or other optical properties exhibited by the electrochromic devices incorporating $\varepsilon\text{-}WO_3$ are driven by the asymmetric ferroelectric properties associated with the unique crystal structure of $\varepsilon\text{-}WO_3$. It is further believed that the electrochromic reversibility is coupled with the polarization switching of the material. More specifically, in the context of the present disclosure, the term "ferroelectric material" relates to a material that exhibits, over a range of temperature, a spontaneous electric polarization that can be reversed or reoriented (known as "switching"), usually, by application of an electric field. Regions with different orientations of the polarization vector can coexist within a ferroelectric sample.

Electrochromic devices set forth herein advantageously exhibit both electrochromic and ferroelectric properties suitable for use in a variety of switching applications. Moreover, the need for ion storage layer(s), electrolytic layer(s), and/or intercalation of metal ions, such as lithium ions ($Li^+$), in the $\varepsilon\text{-}WO_3$ is obviated.

The layer of $WO_3$ is in electrical communication with the plurality of electrodes, which, for example, can comprise or consist of at least a first electrode and a second electrode. The first electrode and the second electrode can include a cathode and an anode. The layer of $WO_3$ is optionally disposed between the first and second electrodes. Alternately, the layer of $WO_3$ is optionally disposed on the first and second electrodes. The first and second electrodes can form an electrode set or pair configured to bias electrical current through the device in a forward or reverse direction, and, in certain cases switches between the forward and reverse directions.

In certain embodiments, the first and second electrodes form a set of interdigitated electrodes. The term "interdigitated" as used herein, refers to, at least two complementarily-shaped electrodes, wherein "branches" or "fingers" of each electrode are disposed in an alternating manner, each of the alternating branches or fingers separated from adjacent branches or fingers by an interelectrode space. In some cases, the electrodes described herein may be an interdigitated structure of at least two working electrodes. For example, the interdigitated electrodes can be an arrangement of electrodes wherein a first working electrode (cathode) is placed next to a second working electrode (anode) in an alternating manner. In some examples, the interdigitated electrodes can include a set of microelectrode fingers (such as from 1 micron to 1000 microns or from 10 microns to 100 microns) separated by an interelectrode space (such as from 1 micron to 1 mm or from 5 microns to 50 microns). The interdigitated electrodes can contain comb, curved, square, rectangular, triangular, hexagonal, or polygonal shaped "fingers" which are arranged in an alternating fashion with respect to one another. It should be understood that other shapes of electrodes may also be suitable for use as interdigitated electrode. The interdigitated electrode arrays are particularly suitable for devices such as windows and displays due to their planar configuration.

The layer of $WO_3$ is disposed on or over portions of each electrode and, in some cases, directly contacts each electrode. FIG. 2 illustrates an exemplary electrochromic device. A plurality of interdigitated electrodes are disposed on a substrate and below the layer of $WO_3$ of the device. The plurality of interdigitated electrodes can substantially cover the substrate and/or layer of $WO_3$. The shape of the substrate and/or layer of $WO_3$ can be a square, rectangular, triangular, hexagonal, or polygonal shape.

In certain embodiments, the electrodes can be configured to form a uniform or substantially uniform color distribution in the layer of $WO_3$. Alternatively, the electrodes can be configured to form a non-uniform color distribution in the layer of $WO_3$. The size, shape, and/or uniformity of the color distribution of the layer of $WO_3$ can be determined via the size, shape, and/or placement of the electrodes being layered, deposited, or coated with ε-WO$_3$, in certain cases. Notably, the layer of WO$_3$ exhibits polarization switching and simultaneously exhibits electrochromic and ferroelectric behavior.

The electrodes can comprise or be formed from any material and/or have any size, shape, property, or other characteristic not inconsistent with the objects of the instant disclosure. In some cases, for example, the electrodes are substantially transparent or translucent, opaque, flexible, or rigid. The electrodes can comprise or be formed from any electrically conductive material, such as a metal or metal oxide. The electrodes can, but do not have to be interdigitated. For example, in some cases, the electrodes are optionally vertically or horizontally aligned and stacked relative to each other with the layer of WO$_3$ being disposed therebetween. Any position or arrangement of electrodes relative to each other and/or relative to the layer of WO$_3$ is contemplated.

Further, the layer of WO$_3$ can comprise, consist, or essentially consist of up to 100% ε-WO$_3$, based on the total weight of the WO$_3$. The ε-phase is an acentric crystal phase that exhibits polarization switching and asymmetric ferroelectric properties. The layer of WO$_3$ can comprise at least about 40% ε-WO$_3$, at least about 45% ε-WO$_3$, at least about 50% ε-WO$_3$, at least about 55% ε-WO$_3$, at least about 60% ε-WO$_3$, at least about 70% ε-WO$_3$, at least about 80% ε-WO$_3$, or at least about 90% ε-WO$_3$, based on the total weight of the WO$_3$. Stated differently, the layer of WO$_3$ can comprise or consist of from about 40% to about 100% ε-WO$_3$, from about 40% to about 90% ε-WO$_3$, from about 40% to about 80% ε-WO$_3$, from about 40% to about 60% ε-WO$_3$, from about 40% to about 50% ε-WO$_3$, from about 45% to about 100% ε-WO$_3$, from about 50% to 100% ε-WO$_3$, or from about 50% and 90% ε-WO$_3$, based on the total weight of the WO$_3$.

In some instances, the layer of WO$_3$ comprises or is formed from nanoparticles of ε-WO$_3$ having an average particle size of up to 100 nm in at least two dimensions. For example, the layer of WO$_3$ can comprise nanoparticles of ε-WO$_3$ having an average particle size of 95 nm or less, 90 nm or less, 85 nm or less, 80 nm or less, 75 nm or less, 70 nm or less, 65 nm or less, 60 nm or less, 50 nm or less, from about 10 nm to 100 nm, or from about 5 nm to 100 nm in at least two dimensions, or any subrange therebetween. That is, the layer of WO$_3$ can comprise nanoparticles of ε-WO$_3$ having an average particle size of from about 10 nm to 50 nm, from about 10 nm to 75 nm, from about 50 nm to 100 nm, or any other subrange not inconsistent with the instant disclosure. Additionally, ε-WO$_3$ particle sizes that are less than about 10 nm in at least two dimensions or greater than about 100 nm in at least two dimensions are contemplated.

Further in this regard, and in other instances, the layer of WO$_3$ comprises or is formed from nanoparticles of ε-WO$_3$ having an average particle size of up to 60 nm in three dimensions. For example, the layer of WO$_3$ can comprise nanoparticles of ε-WO$_3$ having an average particle size of between about 10 nm and 60 nm in at least three dimensions, or any subrange therebetween. That is, the layer of WO$_3$ can comprise or be formed from nanoparticles of ε-WO$_3$ having an average particle size of between about 10 nm and 50 nm, between about 25 nm and 50 nm, between about 40 nm and 60 nm, or any other subrange not inconsistent with the instant disclosure.

Additionally, and in some embodiments, the layer of WO$_3$ comprises pure ε-WO$_3$. Pure ε-WO$_3$ as used herein refers to a layer of WO$_3$ comprising substantially 100% ε-WO$_3$, based on the total weight of the WO$_3$. Said an other way, the layer comprising pure ε-WO$_3$ does not include doped or a mixed-phase WO$_3$.

Alternatively, the layer of WO$_3$ can comprise doped ε-WO$_3$, or a mixed phase of ε-WO$_3$. Where the ε-WO$_3$ is doped, the dopants may include silicon (Si), chromium (Cr), cerium (Ce), a vanadium phosphorus oxide (VPO), or any combination thereof. The layer of WO$_3$ can comprise ε-WO$_3$ doped with any other compound or element not inconsistent with the objects of the instant subject matter. The dopant such as Si or Cr can be present in any suitable amount, based on the end use of the electrochromic device. In certain embodiments, the dopant can be present in an amount of up to 50% by weight, based on the total weight of the layer of WO$_3$. For example, the dopant can be present in an amount of 1% by weight or greater, 2% by weight or greater, 5% by weight or greater, 10% by weight or greater, 15% by weight or greater, 20% by weight or greater, 25% by weight or greater, 30% by weight or greater, 40% by weight or greater, 45% by weight or greater, from 1% to 50% by weight, from 1% to 25% by weight, from 5% to 50% by weight, from 5% to 25% by weight, from 1% to 10% by weight, based on the total weight of the layer of WO$_3$.

Where the ε-WO$_3$ is a mixed phase, the phases other than ε-WO$_3$ present in the WO$_3$ layer can include monoclinic γ-phase, orthorhombic β-phase, tetragonal α-phase, hexagonal phase, triclinic δ-phase, cubic phase, or a mixture thereof. The synthetic method and conditions used can affect the phase and proportion of WO$_3$ present. Polymorphs of WO$_3$ are known in the art. In some examples, ε-WO$_3$ can be present in combination with γ-phase and/or δ-phase. In certain cases, the polarization switching of the ferroelectric domain can be enhanced when a mix phase of ε-WO$_3$ exists, such as combination of ε-WO$_3$ with γ-phase and/or δ-phase exists. In certain embodiments, the phases other than ε-WO$_3$ present can be in an amount of up to 50% by weight, based on the total weight of the layer of WO$_3$. For example, the phases other than ε-WO$_3$ present can be in an amount of 1% by weight or greater, 2% by weight or greater, 5% by weight or greater, 10% by weight or greater, 15% by weight or greater, 20% by weight or greater, 25% by weight or greater, 30% by weight or greater, 40% by weight or greater, 45% by weight or greater, from 1% to 50% by weight, from 1% to 25% by weight, from 5% to 50% by weight, from 5% to 25% by weight, from 1% to 10% by weight, based on the total weight of the layer of WO$_3$.

As described herein, the layer of WO$_3$ is electrochromic, and switches between a colored state and a bleached state in response to an applied bias between the electrodes, which, in some cases are interdigitated. In the colored state, current is being passed through the electrodes and the layer of WO$_3$ may exhibit a substantially black color, a substantially blue color, a substantially green color, or a substantially yellow color in some cases. In the bleached state, current is not being passed through the electrodes and the layer of WO$_3$ retains its original color. For example, and in some cases, biasing the electrodes in the forward direction causes the layer of WO$_3$ to assume a first coloration scheme whereas biasing the electrodes in the opposite, reverse direction causes the layer of WO$_3$ to assume a second coloration scheme. The first coloration scheme can comprise coloration being localized proximate to the first electrode and the second coloration scheme can comprise coloration being localized proximate to the second electrode. Biasing the current can induce coloration at a desired electrode. Additionally, switching the current can switch a location of the electrically induced or triggered coloration. As coloration in the layer of $WO_3$ is reversible, removal of the electrical bias will return the layer of $WO_3$ to its original bleached state. In the colored state, the layer of $WO_3$ can exhibit a uniform or substantially uniform color distribution. Alternatively, the layer of $WO_3$ can exhibit a non-uniform color distribution. The size, shape, and/or uniformity of the color distribution can be determined via the size, shape, and/or placement of the electrodes being layered, deposited, or coated with $\varepsilon$-$WO_3$, in certain cases.

Notably, in some embodiments, the layer of $WO_3$ comprising $\varepsilon$-$WO_3$ does not include intercalated ions, particularly intercalated ions of a particular type. For example, in some instances, the crystal structure $\varepsilon$-$WO_3$ present in a layer described herein is devoid or otherwise not intercalated with lithium ions, or any other metal ions for effecting a color or color change of the layer of $WO_3$.

The electrochromic devices described herein can further comprise a substrate. The electrodes and/or layer of $WO_3$ can, singly or combined, be disposed on or over the substrate. In some embodiments, the substrate can be transparent or opaque. The substrate can be formed from any material not inconsistent with the objects of the instant disclosure. For example, and in some cases, the substrate is formed from glass, ceramic, paper, plastic, or combinations thereof. The substrate can be flexible or rigid. The substrate can comprise any size and shape not inconsistent with the objects of the instant disclosure.

The electrochromic devices described herein can be used in windows such as smart windows. In particular, electrochromic windows can be adjusted to control the amount of light and heat passing through them. In some embodiments, the electrochromic devices described herein can comprise or otherwise be used and incorporated in electrochromic mirrors or displays. In further instances, the electrochromic devices described herein can comprise or otherwise be used and incorporated in non-volatile memory elements. The electrochromic devices are suitable for use as electrochromic mirrors such as rearview mirrors (e.g., truck mirrors, interior and exterior mirrors for motor vehicles), architectural mirrors or specialty mirrors, like those useful in aeronautical, periscopic or dental and medical applications. In addition, the electrochromic devices can be used as electrochromic glazings (e.g., architectural glazings, like those useful in the home, office or other edifice; aeronautical glazings, such as those which may be useful in aircraft; or vehicular glazings, for instance, windows, like windshields, side windows and backlights, sun roofs, sun visors or shade bands); electrochromic optically attenuating contrast filters, such as contrast enhancement filters, suitable for use in connection with cathode ray tube monitors and the like; electrochromic privacy or security partitions; electrochromic solar panels, such as sky lights; electrochromic information displays; and electrochromic lenses and eye glass, may also benefit from that which is described herein, especially where substantially non-spectral selective coloring is desired.

In addition, the electrochromic devices can be used to provide an "on demand display" for transparent devices such as windows, mirrors, and such the like. The window or mirror construction facilitates placement of displays, indicia and sensors and the like behind the mirror element so that they may be viewed as an "on demand display." As described herein, the electrochromic devices can exhibit a substantially colored state upon the introduction of an applied potential. The coloring capability of these devices may be continuously varied by controlling the magnitude, duration, and polarity of the applied potential introduced thereto.

In further instances, the electrochromic devices described herein can comprise or otherwise be used and incorporated in sensors, for example sensors for detecting acetone in a fluid. Particularly, electrochromic sensors can comprise a substrate, a set of electrodes disposed on or within the substrate, and a layer comprising $\varepsilon$-$WO_3$ disposed in electrical communication with the set of electrodes. The electrochromic sensor is capable of providing a change in color indicating the presence of acetone in the fluid. The electrochromic device can exhibit a limit of detection of 10 parts per million or less.

It is to be understood that the electrochromic devices described herein can comprise, include, consist, or consist essentially of any combination of components or features described herein.

Generally, electrochromic devices such as windows generally comprise up to seven layers of material. Three central layers (ion storage layer, ion conducting layer and electrochromic layer) are sandwiched between two layers of a transparent conductor, all of which are further sandwiched between two layers of glass or plastic. These windows function as the result of transport of charged ions from an ion storage layer, through an ion conducting layer into an electrochromic layer by applying certain voltage. The presence of the ions in the electrochromic layer changes its optical properties, causing it to absorb visible light, the result of which is to darken ("unbleach") the window. To reverse the process, the voltage is reversed, driving the ions in the opposite direction, out of the electrochromic layer, through the ion conducting layer, and back into the ion storage layer. As the ions migrate out of the electrochromic layer, it brightens (or "bleaches"), and the window becomes transparent again.

Notably, as indicated herein, the electrochromic devices described herein do not include an ion storage layer or an ion conducting or electrolytic layer. The electrochromic devices function due to shifts in the negative z direction in $\varepsilon$-$WO_3$ are larger than those in the positive z direction. Because of the inequality of shifts in the z direction, a net spontaneous polarization develops along the c axis of $\varepsilon$-$WO_3$ which is thought to give the material ferroelectric properties. In ferroelectric materials, there exists a switching current that is associated with the alignment of ferroelectric domains. Physically, this switching current can be related to the required voltage needed to reorient and align the electrical dipoles within the material to that of the external electric field. Similar to electrochromism, ferroelectricity involves a sustainable and reversible change of the material's electrical dipole when an electric field is applied to the material. In the case of $\varepsilon$-$WO_3$ which is both an electrochromic material as well as a ferroelectric material due to its electronic band structure and crystallographic asymmetry respectively, a coloration effect under the application of an external electric field which is entirely reversible can be obtained. The electric field can be generated by an applied voltage of 10 V or greater, such as 30 V or greater, 40 V or greater, 50 V or greater, 60 V or greater, 70 V or greater, 80 V or greater, or from 30 V to 80 V. The time required to effect a color change such as transition from a bleached state to a colored state appears can be related to the supplied voltage. In some instances, the time can be 30 minutes or less, 20 minutes or less, 10 minutes of less, 5 minutes or less, 2 minutes or less, 1 minute or less, 30 seconds or less, 20 seconds or less, 10 seconds or less, within applying a voltage to the $\varepsilon$-$WO_3$ material. The reversible coloration effect exhibited by ε-WO$_3$ is a result of the ferroelectric polarization and not due to interaction of ions.

Methods of Making Electrochromic Devices

In a further aspect, methods of making electrochromic devices are provided. The methods set forth herein can be used to provide or fabricate any of the electrochromic devices described herein. For example, and in some embodiments, a method of making an electrochromic device comprises forming a layer of WO$_3$ and placing the layer of WO$_3$ in electrical communication with a set of electrodes such that the layer of WO$_3$ exhibits polarization switching.

For example, the layer of WO$_3$ can be deposited or otherwise formed on or over one or more electrodes and/or optionally on or over a substrate overlying, underlying, or disposed adjacent to the electrodes. The electrodes and/or the layer of WO$_3$ can each be disposed on or over the substrate, where desired. The electrodes and/or the layer of WO$_3$ can but do not have to contact the substrate directly.

Notably, the layer of WO$_3$ primarily contains ε-WO$_3$, meaning that the majority component of the WO$_3$ layer is ε-WO$_3$. In certain cases, the layer of WO$_3$ is formed via flame spray pyrolysis (FSP). The size of particles formed in FSP depend on ODOP (one droplet to one particle), ODMP (one droplet to multiple particles) or gas phase transition. For homogenous solutions, ODOP results in formation of uniform particle sizes in submicron or micron range, while ODMP and gas phase result in nanosized particles. The gas phase mechanism is preferred when the WO$_3$ source compound (precursor) is combustible. For example, due to the combustible nature of tungsten-isopropoxide, gas phase mechanism is preferred by FSP.

Tungsten isopropoxide is combustible at 500° C., the combustion gives rise to an exothermic reaction and leads to formation of tungsten vapors and decomposed organic precursors. The vapors are readily oxidized into WO$_3$ vapors, which then undergo nucleation and agglomeration. The Cr-doped powders are vaporized into W vapors at ~600° C., the decomposition of the precursor is an endothermic reaction, and follow the same route as W vapors generated from tungsten isopropoxide solution.

The final size of the crystallites depends on the residence time and operating parameters, these are precursor composition, fuel and oxidant flow rate and size of droplet and flame. A direct relation between oxidant flow-rate has been noticed for Cr-doped particles.

The formation of ε-WO$_3$ particles can further be described as follows. The precursor solutions upon entering the flame lead to atomization and oxidation of W atoms. The existence of large temperature gradient prefers the formation of ε-WO$_3$ particles. The particles undergo nucleation, coagulation, and agglomeration. The particle size depends on the residence time, which relates to the time the particles spend in the chamber upon atomization. A shorter residence time gives rise to small particle sizes and thus a stabilized ε-WO$_3$ is received. The formation of γ phase occurs once the critical crystallite size for the particles is crossed, this critical size can be calculated using a heuristic model. In this disclosure, the relative high boiling points of iso-propanol (82.6° C.) and ethanol (78.37° C.) ensure less residence time and hence result in formation of ε-WO$_3$ particles. The percentage of E phase is generally higher in pure WO$_3$ compared to Cr-doped WO$_3$. The concentration of metal ions in the isopropoxide solution may be lower compared to Cr doped solution. However, the source compound (precursor) can also play a role in formation of higher E phase content. The exothermic reaction from the combustion of tungsten isopropoxide gives rise to a higher temperature gradient compared to the endothermic decomposition of ammonium salt, for example. The high temperature gradient favors the formation of ε-phase by delaying the nucleation and yielding lower residence time.

Heat treatment, such as calcination, of the synthesized particles can lead to grain coarsening and an increase in crystallite size. In some cases, pure WO$_3$ powders may exhibit a drop in % ε-WO$_3$ content. Once the crystallites for ε-phase cross the critical size barrier, a transformation into γ phase occurred.

In certain embodiments, methods of making a WO$_3$ electrochromic material can include dissolving a tungsten trioxide source compound in a solvent comprising an alcohol to form a liquid feed stream. In some cases, the tungsten trioxide source compound comprises a tungsten compound which exhibits an exothermic oxidative decomposition. For example, the tungsten trioxide source compound can comprise tungsten isopropoxide. Other examples of tungsten trioxide source compound can include any tungsten salt such as tungsten alkoxide or ammonium tungstate. The solvent can be a high boiling solvent such as an alcohol (e.g., ethanol or methanol).

The method can further comprise atomizing the liquid feed stream within an oxygen-containing gas to form an aerosol followed by combusting the tungsten trioxide source compound, thereby forming the WO$_3$ electrochromic material, wherein the WO$_3$ electrochromic material comprises ε-WO$_3$ nanoparticles. As described herein, the method can further comprise rapid solidification of the ε-WO$_3$ nanoparticles after combustion, calcining the ε-WO$_3$ nanoparticles, or a combination thereof. The WO$_3$ electrochromic material formed can comprise at least 40% by weight ε-WO$_3$ nanoparticles, such as from 40% to 50% by weight ε-WO$_3$ nanoparticles, using the FSP method.

In other cases, the layer of WO$_3$ can be formed via laser pyrolysis. Still further, and in some cases, the layer of WO$_3$ can be formed via high energy ball milling or a rapid solidification process.

The methods for making the electrochromic devices can further include depositing a layer comprising the synthesized ε-WO$_3$ nanoparticles over an electrode. Preferably, the electrode is an interdigitated electrode. Any process not inconsistent with the objects of the instant subject matter can be used to form the layer of WO$_3$, which primarily contains ε-WO$_3$, on or over the electrodes and/or other surface or substrate of the device.

It is to be understood that the methods of making electrochromic devices described herein can include any combination of components, features, and/or processes described herein.

Methods of Using Electrochromic Devices

In some aspects, methods for detecting acetone in a fluid using the electrochromic devices described herein are provided. The method can include contacting an electrochromic device with the fluid; and observing a change in color of the ε-WO$_3$ layer, wherein the change in color indicates the presence of acetone in the fluid. As described herein, the electrochromic device can comprise a substrate, a set of electrodes disposed on or within the substrate, and a layer comprising ε-WO$_3$ disposed in electrical communication with the set of electrodes. Using the methods disclosed herein, a concentration of acetone can be measured.

The observed or measured response of the electrochromic device to the presence of acetone can be a color change. The acentric structure of ε-WO$_3$ plays a role on the selective detection of acetone. In particular, the ε-WO$_3$ is ferroelectric which has a spontaneous electric dipole moment. The polarity comes from the displacement of tungsten atoms from the center of each [$WO_6$] octahedra. Acetone has a much larger dipole moment than any other gas. As a consequence, the interaction between the ε-$WO_3$ surface dipole and acetone molecules may be much stronger than any other gas, leading to the observed selectivity to acetone detection. Notably, the observed or measured response of the electrochromic device to the presence of acetone is due to a color change and not a change in an electrical property of the ε-$WO_3$ layer (for example, conductance or resistance).

An observed or measured concentration of acetone can be correlated with a subject's medical condition, such as diabetes, ketosis, or other abnormal acetone concentration conditions.

The ε-$WO_3$ ferroelectric materials described herein can further be used in quantum information including cooling systems, energy storage units, sensing devices, and computer memory. In certain embodiments, the ε-$WO_3$ can be used for ion-based computing in quantum memory devices or for ferroelectric-superconductor heterostructure to provide a high speed, coherent, nonvolatile switch in a solid state quantum computing system.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Flame Spray Pyrolysis Synthesized ε-$WO_3$

Figure 1:
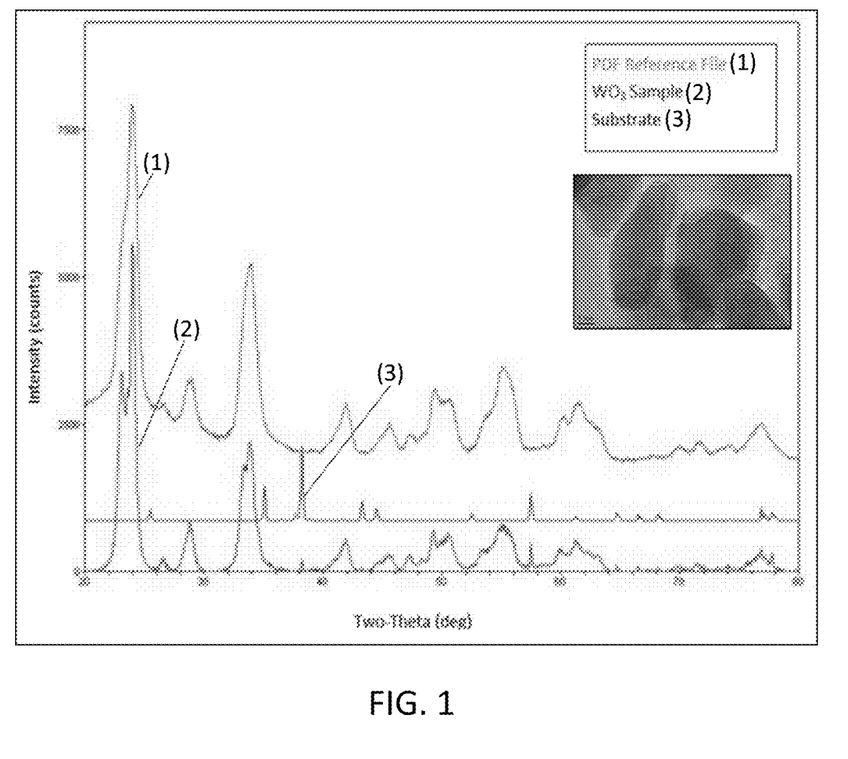
FIG. 1 is a graphical illustration of comparative X-Ray Diffraction (XRD) spectra of tungsten trioxide films.

The ε-$WO_3$ was fabricated using a flame spray pyrolysis device (e.g., TETHIS NPSIO). X-ray diffraction (XRD) of the synthesized material was performed using a Rigaku (Ultima 3) testing apparatus. FIG. 1 shows comparative XRD spectra of the as received unheated flame spray pyrolysis material (2), the powder diffraction file of a reference sample (1), and the substrate (3). The synthesized material's XRD spectrum closely matches the reference sample, as seen in FIG. 1. Additionally, FIG. 1 includes an inlay of a transmission electron microscopy (TEM) image or micrograph of the synthesized nanopowder. High resolution transmission TEM was carried out in a Hitachi H-9500 instrument. The as-synthesized powder was found to be nanocrystalline (see inset in FIG. 1).

The $WO_3$ films were prepared by drop coating a mixture of flame spray pyrolysis synthesized ε-$WO_3$ and 1-heptanol (purity 99%, Sigma Aldrich) onto a substrate of alumina (CoorsTek ADS-996) with gold interdigitated electrodes (Case Western EDC #102). Conductive silver paint (PELCO 16062) was then applied to the contact pads to promote electrical contact. The gold fingers were approximately 250 μm wide with an approximately 250 μm gap in between and the overall sensing area was about 10 cm by 10 cm. Electrical polarization was achieved through the use of a Keithley 6517a voltage generator.

Figure 2A:
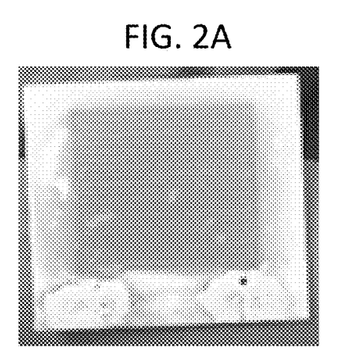
FIGS. 2A-2D are photographs of tungsten trioxide films according to embodiments of the presently disclosed subject matter.
Figure 2B:
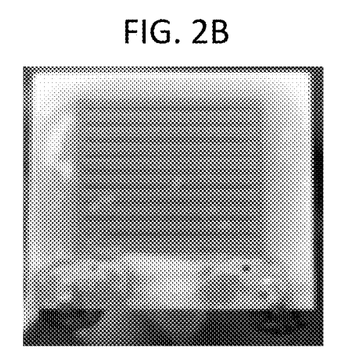
Figure 2C:
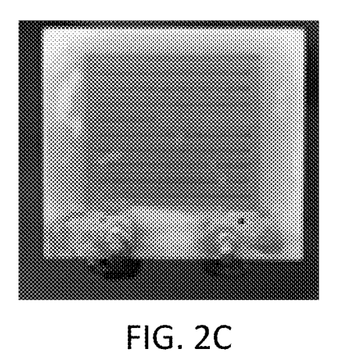
Figure 2D:
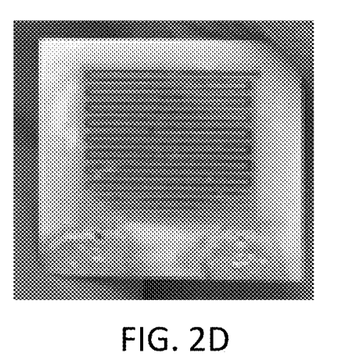

Before applying an external voltage, the color of the film on the electrode is originally a dark yellow-brown. While not completely transparent, it is translucent enough to see the shape of the electrode below it. FIG. 2A shows an image of the electrode before testing. After a voltage is applied to the electrode, one can observe a dark coloration beginning to form on the film gradually. It is interesting to note that this coloration does not persist through the entire film, see FIG. 2B, but is rather confined locally to the electrode with the black (−) voltage. If polarity of the voltage source is then switched, which is represented by a physically swapping of the black and red connectors, the coloration on the right electrode begins to vanish and the coloration appears now on the left electrode, which now has the black (−) voltage. Upon switching the electrodes a third time, the coloration once again disappears from the left side and reappears on the right side with the black (−) voltage. If the electrodes are left to sit in ambient air overnight, the coloration on the film completely disappears and the film returns to its original bleached state. FIG. 2A is a photograph of the film before testing, FIG. 2B is a photograph of the film after the first poling, FIG. 2C is after reverse poling, and FIG. 2D is a saturated film at +100 V.

Due to its perovskite like structure, $WO_3$ is capable of being intercalated by a number of different ions including gold and silver. However, when these atoms are included in the $WO_3$ crystal structure, the $WO_3$ structure is distorted. These distortions can be viewed and quantified through the use of Raman Spectroscopy. To further investigate the cause of this coloration, Raman spectroscopy (Thermo Scientific DXR) was used to compare the Raman shift between the bleached and colored sample.

Figure 3:
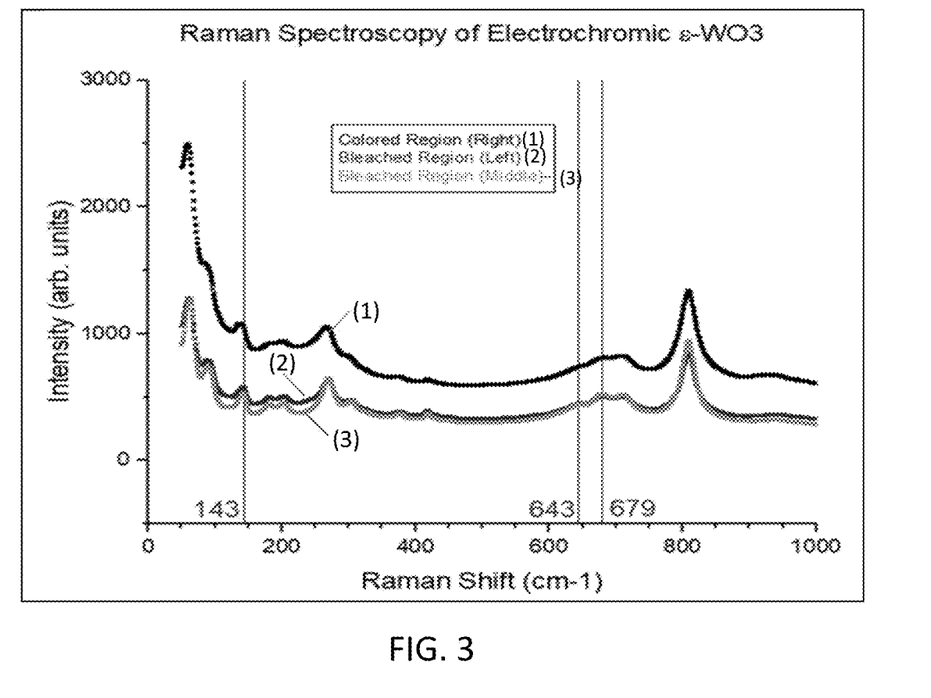
FIG. 3 is a graphical illustration of Raman spectra data obtained for electrochromic glasses comprising tungsten trioxide films according to embodiments of the presently disclosed subject matter.

FIG. 3 shows a comparative Raman plot in a colored region and two uncolored regions. Looking at FIG. 3, one can see peaks at 143, 643, and 679 cm·1, which are the characteristic peaks of the £ phase. Aside from a change in the intensity of the black area, there is no notable change between the three plots. Not intending to be bound by theory, it is believed that it is not intercalation of the electrode ions into the $WO_3$ structure which is causing this change.

Furthermore, although $WO_3$ (in general, not the specific ε-$WO_3$ layers described herein) is a well-known electrochromic material, it typically requires a solid or liquid electrolyte to promote the transfer of ions from the ionic layer into the $WO_3$. However, despite the absence of this layer, ε-$WO_3$ containing layers described herein still exhibit a reversible electrochromic effect.

It is believed that the coloration effect observed here is a result of the material's ferroelectric properties and not of the anticipated intercalation. Without being bound by theory, it is believed that the redistribution of charge that comes about because of the ion flow during intercalation induces electrochromic behavior. Similarly, in ferroelectric materials, when a device is poled, redistribution in the crystal of the electrical dipoles is obtained. While these are two vastly different mechanisms, the overall effect, i.e., the redistribution of charge, is believed by the present inventors to be the same. It is believed that this redistribution of electrical dipoles that comes about during ferroelectric domain inversion is the underlying cause of this coloration change.

The presence of a reversible electrochromic effect on thick films of flame spray pyrolysis synthesized ε-$WO_3$ on gold interdigitated electrodes is described above. Despite the absence of a solid or liquid electrolytic layer, the system appears to undergo an oxidation and reduction style reaction that is not related to the intercalation of the electrode material into the $WO_3$ crystal structure.

Furthermore, while this coloration is reversible, it does not persist more than a day suggesting that the excess electrons are redistributed either throughout the system or with the ambient environment. The appearance of this coloration while imaging in a scanning electron microscope in a very high vacuum debunks the idea that it is the surface adsorbents or atmospheric water forming $HxWO_3$ tungsten bronzes. Again not intending to be bound by theory, it is believed that the coloration change occurs due to a redistribution of charge resulting from ferroelectric domain inversion and a redistribution of its electrical dipoles.

Devices and methods described herein have the potential to revolutionize the design of $WO_3$ electrochromic glass, including by eliminating the need for both an ionic layer as well as an electrolytic layer. Benefits of devices and methods described herein include the environmental benefit of no longer using lithium based tungsten bronzes. The use of the polarization switching properties of this polymorph of $WO_3$ in non-volatile memory devices is also contemplated herein.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An electrochromic device comprising:
    a substrate;
    a set of electrodes disposed on or within the substrate; and
    a layer comprising $\varepsilon$-$WO_3$ disposed in electrical communication with the set of electrodes,
    wherein the layer of $\varepsilon$-$WO_3$ exhibits polarization switching.

2. The device of claim 1, wherein the set of electrodes are interdigitated.

3. The device of claim 1, wherein the $\varepsilon$-$WO_3$ comprises nanoparticles having an average particle size of from 10 nm to 100 nm.

4. The device of claim 1, wherein the $\varepsilon$-$WO_3$ comprises pure $\varepsilon$-$WO_3$, doped $\varepsilon$-$WO_3$, or a mixed phase of $\varepsilon$-$WO_3$.

5. The device of claim 1, wherein the substrate comprises a glass, ceramic, or plastic.

6. The device of claim 5, wherein the substrate is transparent.

7. The device of claim 1, wherein upon application of a potential bias, the $\varepsilon$-$WO_3$ exhibits a color change.

8. The device of claim 7, wherein the $\varepsilon$-$WO_3$ switches between a colored state and a bleached state.

9. The device of claim 8, wherein the layer of $\varepsilon$-$WO_3$, in the colored state, exhibits a uniform or substantially uniform color distribution.

10. The device of claim 1, wherein the device is a window, display, mirror, non-volatile memory element, or sensor.

* * * * *